(12) United States Patent
Gaillard et al.

(10) Patent No.: US 9,084,803 B2
(45) Date of Patent: Jul. 21, 2015

(54) THERAPEUTIC USES OF GLUTATHIONE MIMICS

(75) Inventors: Elizabeth R. Gaillard, DeKalb, IL (US); James P. Dillon, New York, NY (US)

(73) Assignee: Board of Trustees of Northern Illinois University, DeKalb, IL (US)

(*) Notice: Subject to any disclaimer, the term of this patent is extended or adjusted under 35 U.S.C. 154(b) by 1458 days.

(21) Appl. No.: 12/163,192

(22) Filed: Jun. 27, 2008

(65) Prior Publication Data

US 2009/0005349 A1 Jan. 1, 2009

Related U.S. Application Data

(60) Provisional application No. 60/946,999, filed on Jun. 29, 2007.

(51) Int. Cl.
*A01N 57/00* (2006.01)
*A61K 31/66* (2006.01)
*A61K 31/661* (2006.01)

(52) U.S. Cl.
CPC .................................. *A61K 31/661* (2013.01)

(58) Field of Classification Search
None
See application file for complete search history.

(56) References Cited

U.S. PATENT DOCUMENTS

| | | | |
|---|---|---|---|
| 4,970,212 A | 11/1990 | Nowicky | |
| 5,686,450 A | 11/1997 | Hellberg et al. | |
| 6,340,746 B1 | 1/2002 | Roberts et al. | |
| 6,429,219 B1 | 8/2002 | Pearson et al. | |
| 6,558,696 B1 | 5/2003 | Hille et al. | |
| 6,841,536 B2 | 1/2005 | Roberts et al. | |
| 2007/0212339 A1 | 9/2007 | Ansorge et al. | |
| 2009/0005349 A1 | 1/2009 | Gaillard et al. | |
| 2009/0069249 A1 | 3/2009 | Nagasawa et al. | |
| 2009/0239817 A1 | 9/2009 | Walker et al. | |

FOREIGN PATENT DOCUMENTS

| | | |
|---|---|---|
| DE | 19906977 C1 | 6/2000 |
| WO | WO 96/31212 | 10/1996 |

OTHER PUBLICATIONS

Binkley "Preparation and Properties of S-Phosphocysteine," J Biol Chem. Mar. 1952;195(1):283-5.*
Mukaiyama (Tetrahedron 55 (1999) 8609-8670)).*
Aruoma et al., "The antioxidant action of N-acetylcysteine: Its reaction with hydrogen peroxide, hydroxyl radical, superoxide, and hypochlorous acid," Free Radical Biology and Medicine, vol. 6, Issue 6, 593-597, 1989 (abstract only).
Chae et al. "Dimerization of thiol-specific antioxidant and the essential role of cysteine 47," Proc. Natl. Acad. Sci. USA, vol. 91, 7022-7026, Jul. 1994.
Guan et al., "Evidence for Protein-tyrosine-phosphatase Catalysis Proceeding via a Cysteine-Phosphate Intermediate," The Journal of Biological Chemistry, vol. 266, No. 26 Issue Sep. 15, 1991, 17026-17030.
Hwang et al. "Efficient Synthesis of Phosphorylated Prodrugs with Bis(POM)-phosphoryl Chloride," Organic Letters vol. 6, No. 10, 1555-1556, 2004.
Aruoma et al., "The Antioxidant Action of N-Acetylcysteine: Its Reaction with Hydrogen Peroxide, Hydroxyl Radical, Superoxide, and Hypochlorous Acid," *Free Radical Biol & Med.*, 6: 593-597 (1989).
Cui et al., "Synthesis and preliminary evaluation of anti-HIV agent AZT prodrug," *Yao Xue Xue Bao*, 46(8): 1015-8 (2011) Abstract.
Fuchs et al., "Redox signaling and reactive oxygen species in hypoxic pulmonary vasoconstriction," *Respir.Physiol.Neurobiol.*, 174(3): 282-91 (2010) Abstract.
Khandazhinskaya et al., "Anti-HIV therapy with AZT prodrugs: AZT phosphonate derivatives, current state and prospects," *Expert Opin. Drug Metab. Toxicol.* 6(6): 701-714 (2010).
Li et al., "Regional Differences in Cystine Accumulation Point to a Sutural Delivery Pathway to the Lens Core," *IOVS*, 48(3): 1253-1260 (2007).
Sui et al., "Effect of glutathione peroxidase mimic ebselen (PZ51) on endothelium and vascular structure of stroke—prone spontaneously hypertensive rats," *Blood Pressure*, 14(6): 366-72 (2005) Abstract.
Yuan et al., "Antioxidant activity and cytoprotective effect of j-carrageenan oligosaccharides and their different derivatives," *Bioorg. Med. Chem. Lett.*, 16: 1329-1334 (2006).
"Human Radiation Injury," Edited by Dennis C. Shrieve, Jay Loeffler, p. 48 (2010).

* cited by examiner

*Primary Examiner* — Jeffrey S Lundgren
*Assistant Examiner* — William Lee
(74) *Attorney, Agent, or Firm* — Barnes & Thornburg LLP; Alice O. Martin

(57) ABSTRACT

A prodrug having antioxidant activity, including a phosphorylated compound having a thiol group. A method of treating oxidative stress by administering a prodrug of a phosphorylated compound including a thiol group, removing a phosphate group of the prodrug, and treating oxidative stress. A method of increasing bioavailability of a thiol compound by creating a prodrug by phosphorylating a thiol compound, administering the prodrug, preventing first pass metabolism of the prodrug, removing a phosphate group from the prodrug, and providing active drug to a site in need of therapy from oxidative stress. A method of preventing radiation damage to healthy tissue by administering a prodrug comprising a phosphorylated compound including a thiol group, removing a phosphate group of the prodrug to provide active drug, and preventing radiation damage to healthy tissue.

7 Claims, 21 Drawing Sheets

THERAPEUTIC USES OF GLUTATHIONE MIMICS

CROSS-REFERENCE TO RELATED APPLICATIONS

This application claims the benefit of priority under 35 U.S.C. Section 119(e) of U.S. Provisional Patent Application No. 60/946,999, filed Jun. 29, 2007, which is incorporated herein by reference.

BACKGROUND OF THE INVENTION (1) Field of the Invention

The present invention relates to phosphorylated antioxidant prodrugs. In particular, the present invention relates to the administration of phosphorylated derivatives of cysteine and glutathione as antioxidants for disease prevention and treatment.

(2) Description of Related Art

Oxidative stress is involved in numerous acute and chronic disorders leading to severe biological dysfunction. It is caused by an imbalance between the production of reactive forms of oxygen and a biological system's ability to readily detoxify the reactive intermediates or easily repair the resulting damage. The damage is mediated by short lived oxygen derived components called reactive oxygen species (ROS). ROS is a broad term that includes superoxide anion radicals ($O_2^-$), singlet oxygen ($^1O_2$), hydrogen peroxide ($H_2O_2$), and hydroxyl radicals ($OH^-$). ROS is ubiquitous in all aerobic cells in stasis with the biochemical antioxidants. However, abnormally high production of ROS disrupts the balance with antioxidants leading to oxidative stress. Research over the years has shown that oxidative stress can be the major cause for aging and diseases such as cardio vascular diseases, pulmonary diseases, diabetes, neuro-degenerative diseases, and age related macular degeneration (ARMD). The human body's naturally occurring defense mechanisms against these ROS involve both enzymes and small molecular weight antioxidants.

Some examples of small molecular weight antioxidants are ascorbic acid (Vitamin C), vitamin E, beta-carotene, as well as glutathione, which contain thiol functionality. These compounds scavenge ROS and thereby diminish damage to biological tissues. Glutathione is produced naturally in the liver from amino acids L-cysteine, L-glutamate and glycine. However, during high levels of oxidative stress, naturally produced levels of glutathione may not be enough to prevent damage to the body. Blood serum levels, and thus bioavailability to tissue, can be increased by dietary supplementation. However, glutathione supplementation is not possible as it is a tripeptide and when ingested it is hydrolyzed to its constituent amino acids by gastric acid. Even if injected, the intact molecule does not readily pass through cell membranes and is therefore unavailable to diseased tissue.

During the Cold War, the United States government developed thousands of compounds with the prefix WR (Walter Reed). These are thiol compounds that are capped with a phosphate group, called a phosphorothioate. The intended use of these compounds was that if troops were caught in a nuclear attack which causes massive formation of ROS, they could ingest these compounds. The compounds are unique in that the active component, the thiol, is not released until the compound enters a cell and interacts with the enzyme alkaline phosphatase. Such thiol compounds have not included glutathione.

Amifostine is one radioprotectant that is currently administered to patients that is converted into the free thiol WR-1065. One of the disadvantages of the use of amifostine is the easy ability to overdose. The amount of the drug that must be administered in order to achieve the required amount of bioavailability is very large. It would therefore be advantageous to develop a radioprotectant that does not require large doses to be effective and reduce the risk of overdose.

There are several examples of compounds that have been administered as antioxidants or to elevate natural levels of glutathione. For example, acetylcysteine, which is the N-acetyl derivative of the amino acid L-cysteine, is a precursor in the formation of the antioxidant glutathione in the body and has been administered in the form of a solution for inhalation, I.V. injection, and oral solution. Not only does acetylcysteine administration show an increase in glutathione levels, but the thiol group of the acetylcysteine itself confers antioxidant effects and is able to reduce free radicals. Acetylcysteine is most commonly used as a mucolytic and in the management of paracetamol/acetaminophen overdose. Cysteine isopropyl ester has also been used for such indications.

Phosphocysteine has been produced and the structure and physical properties of the molecule have been studied, such as with mass spectrometry. It is an intermediate in reactions such as catalysis of tyrosine-phosphatase and transport mechanisms. There has been no disclosure, however, of any therapeutic uses of phosphocysteine.

While it has been shown that cysteine derivatives can be administered as a supplement to promote glutathione production, there remains no method to administer glutathione directly. Therefore, there is a need for a glutathione compound as well as other antioxidants that will not be metabolized until desired for stabilizing redox stressed diseases.

BRIEF SUMMARY OF THE INVENTION

The present invention provides for a prodrug having antioxidant activity, including a phosphorylated compound having a thiol group.

The present invention also provides for a method of treating oxidative stress by administering a prodrug of a phosphorylated compound including a thiol group, removing a phosphate group of the prodrug, and treating oxidative stress.

The present invention provides for a method of increasing bioavailability of a thiol compound by creating a prodrug by phosphorylating a thiol compound, administering the prodrug, preventing first pass metabolism of the prodrug, removing a phosphate group from the prodrug, and providing active drug to a site in need of therapy from oxidative stress.

The present invention further provides for a method of preventing radiation damage to healthy tissue by administering a prodrug comprising a phosphorylated compound including a thiol group, removing a phosphate group of the prodrug to provide active drug, and preventing radiation damage to healthy tissue.

BRIEF DESCRIPTION ON THE DRAWINGS

Other advantages of the present invention will be readily appreciated as the same becomes better understood by reference to the following detailed description when considered in connection with the accompanying drawings, wherein.

Figure 20:
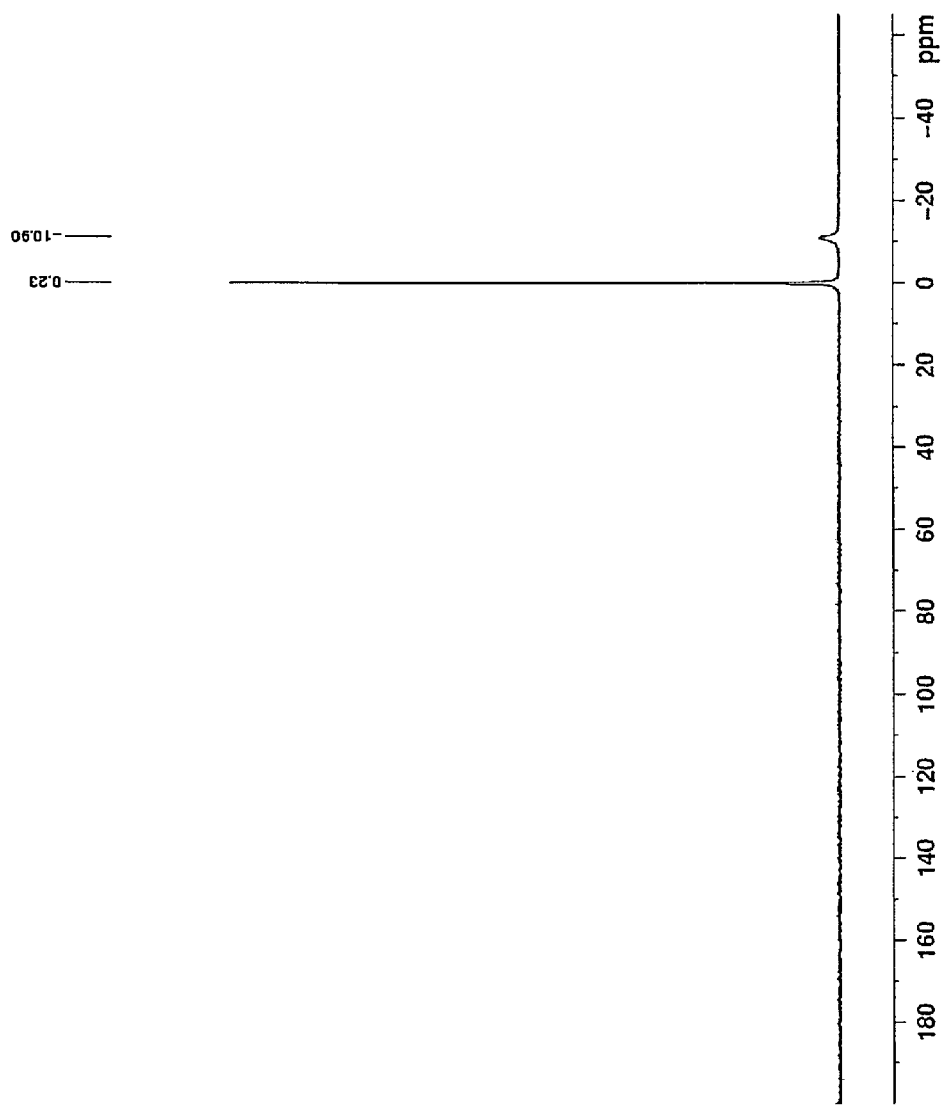
Figure 21:
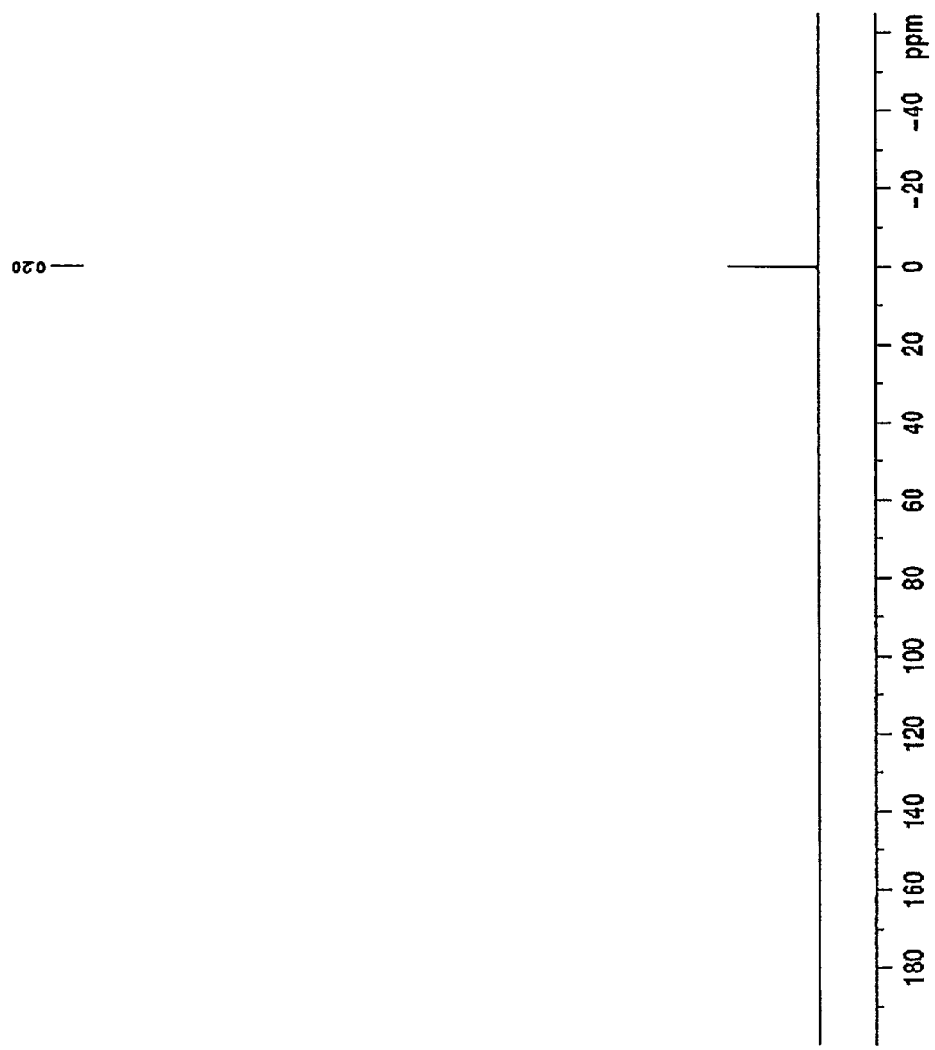

FIG. 20 is a $^{31}$P NMR spectrum for phosphorylated ester NAC after TMSBr reaction, displaying a major peak at 0.23 ppm corresponding to unreacted hydrolyzed DECP and minor peak at −10.90 ppm corresponding to S—P linkage; and FIG. 21 is a $^{31}$P NMR spectrum for DECP phosphorylated ester NAC with alkaline phosphatase. The spectrum displayed a single peak at 0.2 ppm corresponding to free PO$^-_3$.

DETAILED DESCRIPTION

The present invention provides for phosphorylated prodrugs including a thiol group whose antioxidant activity is masked by a phosphate group. Essentially, the present invention is directed to modified natural products, i.e. prodrugs, that are taken up and utilized by cells. These prodrugs are inactive initially when administered and are then activated within a cell, allowing them to be site-targeted therapeutics. Prodrugs require a specific enzyme in order to be activated, and thus can be site-specifically activated where the required enzyme is present. After being taken up by a cell, the phosphate group of the prodrug of the present invention is enzymatically removed, releasing an antioxidant sulfur group. Thus, the antioxidant capacity of the prodrug will only be activated when it is taken up by a cell that has the ability to enzymatically remove the phosphate group, a property which is absent in cancer cells.

As used herein, "prodrug" refers to a pharmacological compound that is in an inactive form when administered, but is metabolized in vivo into an active form of the compound. Prodrugs are generally used to improve bioavailability in oral dosage forms, as well as selectivity of a desired target.

Figure 1:
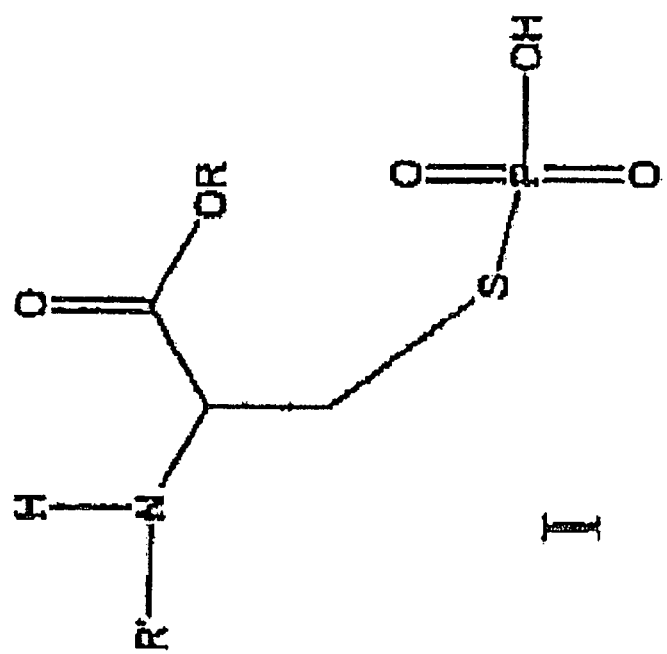
FIG. 1 is a diagram of phosphorylated cysteine (compound I)
Figure 2:
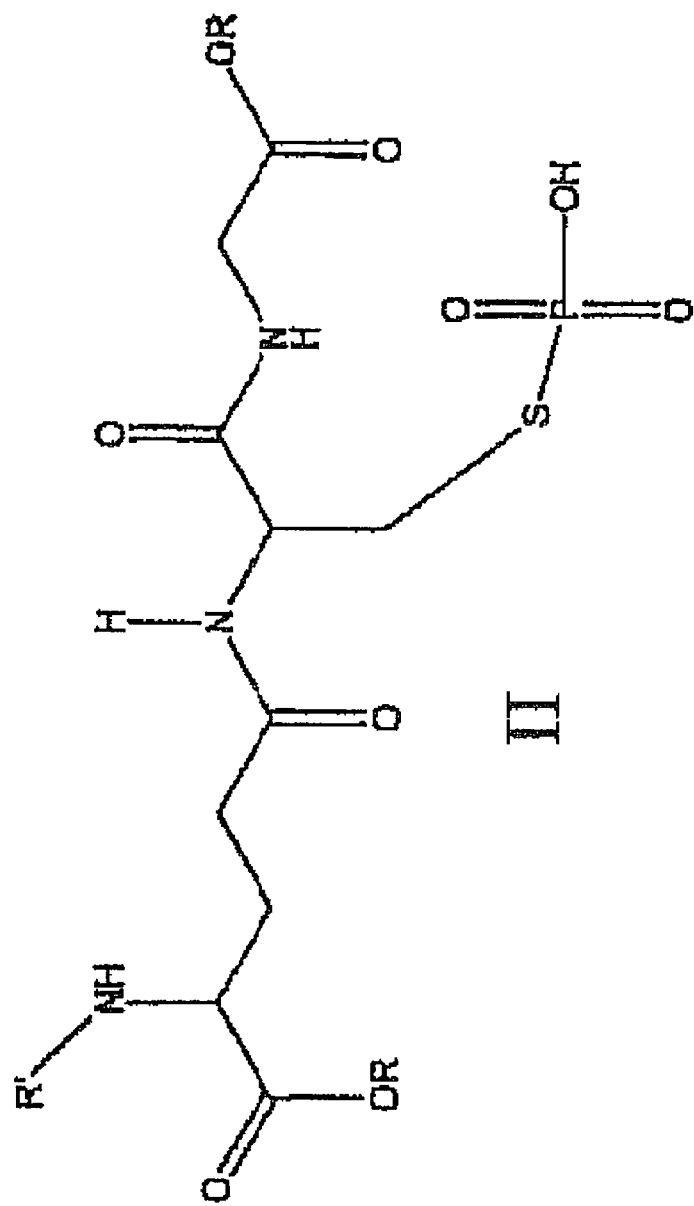
FIG. 2 is a diagram of phosphorylated glutathione (compound II)

The prodrugs of the present invention are further described below and include phosphorylated derivatives of cysteine (I) and glutathione (II) as shown in FIGS. 1 and 2. Neither of these compounds has previously been shown to be administrable with the inclusion of a phosphate group as a therapeutic. The prodrugs include R'=H and various amides such as, but not limited to, acetyl, propyl, or butyl, and R=H, methyl, butyl, propyl, isopropyl, isobutyl, or any other suitable alkyl group. The derivatives of compound I where R' is Ac and R is various esters are synthesized in the same manner, but start with commercially available N-Acetyl cysteine (NAC). Thus, the present invention is specifically directed to S-phosphocysteine, S-phospho-N-acetylcysteine and all esters, as well as S-phosphoglutathione, S-phospho-N-acetylglutathione and all esters. There have been no phosphocysteines previously disclosed including ester or acetate moieties. It is further within the scope of the invention that other antioxidants that are normally metabolized upon administration can be modified in the manner disclosed in the present invention so that administration can become effective. Thus, the present invention is not limited to the examples of phosphorylated derivatives of cysteine and glutathione.

The present invention provides for a method of treating oxidative stress by administering a prodrug of a phosphorylated compound including a thiol group, removing a phosphate group of the prodrug, and treating oxidative stress. The prodrug is administered and the thiol group is protected from first pass metabolism and any other oxidation, and once the prodrug has been taken up by the cell, the phosphate group can be removed and the drug activated to produce anti-oxidant activity to treat oxidative stress. The prodrugs of the present invention are effective oxidative stress reducers and can be used to control oxidative stress in general or treat and/or prevent various diseases and conditions such as, but not limited to, ocular disorders such as glaucoma, cataract and retinal geographic atrophy; atherosclerosis; HIV and AIDS; inflammatory bowel disease; expression of selenoprotein P; lung function; colitis; general disease resistance; general aging; arterial ischemic stroke; chronic obstructive pulmonary disease; cancer such as prostate cancer or gastric cancer; testicular atrophy; schizophrenia; asthma; beta thalassemia major; alcohol metabolism and liver disease; sickle cell disease; celiac disease; neurotoxicity; cystic fibrosis; Parkinson's disease; and Alzheimer's disease.

The present invention further provides for a method of preventing radiation damage to healthy tissue by administering a prodrug comprising a phosphorylated compound including a thiol group, removing a phosphate group of the prodrug to provide active drug, and preventing radiation damage to healthy tissue. The prodrugs of the present invention can be used as radiation protectors that allow healthy tissue to be spared radiation damage. Therefore, the prodrugs can be administered prior to radiation therapy. Further, the prodrugs can be used in cancer treatment radiation therapy. Some of the advantages to using the prodrugs of the present invention for treatment of various diseases are further described below.

There are several advantages to the prodrugs of the present invention. They are more effective than currently available pharmaceutical products because of the elimination of unwanted metabolism. They are virtually non-toxic because they are natural product derivatives. Furthermore, they are relatively inexpensive to produce. The prodrugs are able to target specific cells or tissues for therapeutic purposes and allow for much higher doses of radiation to be used in radiation therapy treatment due to the enhanced protective effect to healthy tissue.

Previously, low bioavailability of thiol containing drugs on administration has been a major concern. Research has repeatedly demonstrated that NAC under goes first pass metabolism, which deacetylates NAC, resulting in major metabolites such as cysteine, cysteine, inorganic sulfites, labile disulphide complexes with plasma and tissue proteins. Thus, the presence of free drug in the systemic circulation is around 9%. This is also the case with intravenous administration where an extensive disulphide formation with plasma and tissue proteins was observed. The protection of the thiol group in the prodrugs of the present invention thus prevents the oxidation of the drug in the intestine and the liver, thereby preventing the formation of metabolites and increasing the bioavailability of drug in the systemic circulation. The phosphate group can then be cleaved by alkaline phosphates in vivo to give the free active form of drug. Therefore, the present invention provides for a method of increasing bioavailability of a thiol compound by creating a prodrug by phosphorylating a thiol compound, administering the prodrug, preventing first pass metabolism of the prodrug, removing a phosphate group from the prodrug, and providing active drug to a site in need of therapy from oxidative stress.

The prodrugs of the present invention are administered and dosed in accordance with good medical practice, talking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art. Preferably, the prodrugs of the present invention are administered at a dose of 200 mg/m$^2$, in a daily injection 15 to 30 minutes prior to radiotherapy, similar to dosing currently recommended for amifostine, the only radioprotectant currently available. As stated above, the amount of the prodrugs administered can also be less than amifostine because of its greater bioavailability.

In the method of the present invention, the compound of the present invention can be administered in various ways. It should be noted that it can be administered as the compound and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, intratonsillar, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

EXAMPLES

Radiation Therapy

Ionizing radiation has been used for decades in the treatment of solid tumors and operates by forming ROS within the tumor causing necrosis. A major liability of this therapy is damage to surrounding normal tissue, which causes severe side effects and limits the amount of radiation used (and therefore, its effectiveness). Most tumors do not express cell-surface alkaline phosphatase, as do surrounding normal tissues, which can convert thiols to the free metabolite. Therefore, a simple method to protect normal tissue is to give the patient a prodrug of the present invention with the phosphorothioate linkage prior to radiation therapy. This allows for a drastic increase in the amount of radiation used with a concomitant increase in effectiveness. Phosphorothioate linkages have already been demonstrated by Applicants to be useful in protecting against the side effects of photodynamic therapy.

Age Related Macular Degeneration

The disruption of the redox state of a cell will lead to its death via apoptosis. The cell is compromised when the supply of glutathione is interrupted. One disease that has been investigated with the prodrug of the present invention is age related macular degeneration (ARMD), which is the leading cause of permanent blindness in the west. One form of ARMD is called dry ARMD, where the retina pigment epithelia die, leading to geographic atrophy. It has been demonstrated that this may be due to the disruption of the redox state. There is no treatment for this disease currently. Therefore, the prodrugs of the present invention can be used in the form of an eyedrop to treat this disease much more effectively.

Disease Caused by Redox Disruption

There are numerous disease processes that are known to result from or include redox disruption including HIV, AIDS, and various forms of cancer. The prodrugs of the present invention can be used to treat these diseases by delivery through a pill, injection, patch, or eye drop wherein the prodrugs eliminate redox disruption.

Example 1

Synthesis of Phosphorylated NAC

N-acetyl-S-phosphocysteine was synthesized according to the procedure followed by Binkely (1954). N-acetyl cysteine (0.5 g) was dissolved in 8 mL of distilled water in an ice bath. The NAC solution was then treated with 0.2 mL of phosphorus oxychloride and with sodium hydroxide to maintain the basic pH of 11. The resulting white solid was dried and re-dissolved in deuterium oxide for $^{31}P$, $^{13}C$ and $^{1}H$ NMR analysis. After analysis, the sample was dried, re-suspended in water, and treated with 1 mg (10 units) of alkaline phosphatase, and stirred for 2 hours. The solution was dried and resuspended in deuterium oxide for NMR analysis.

Figure 3:
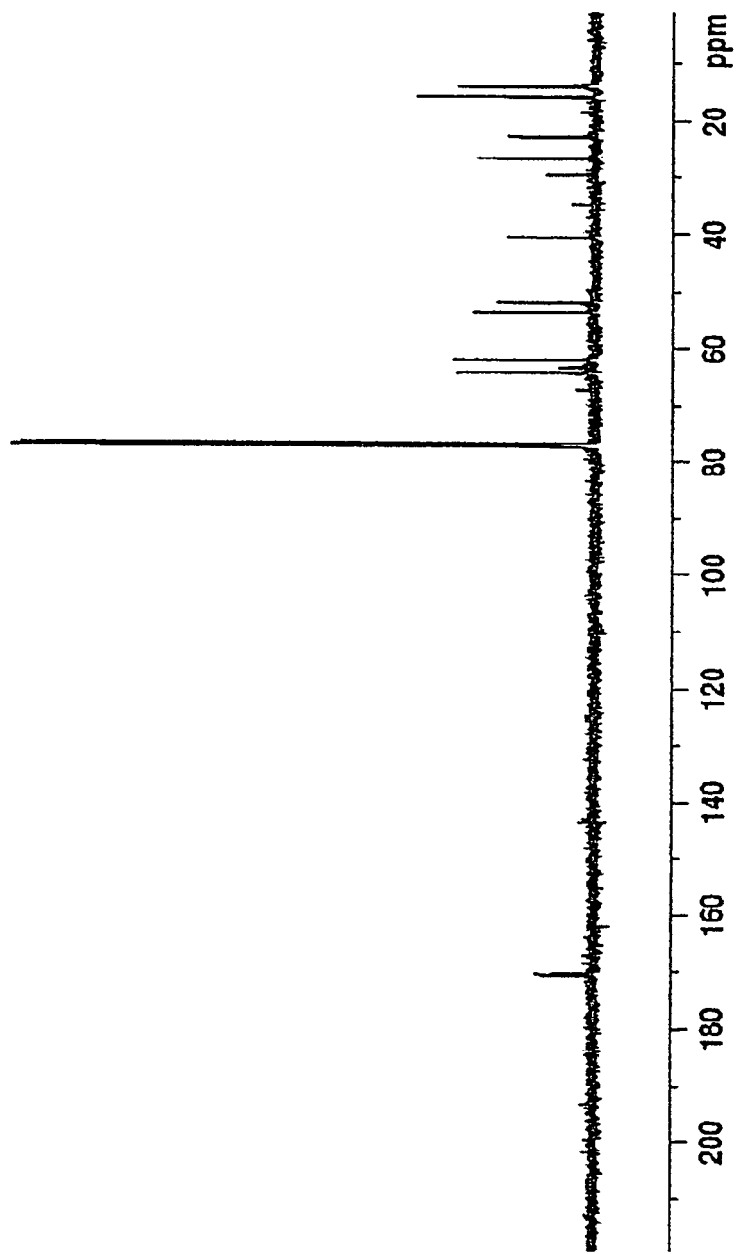
FIG. 3 is a $^{13}$C NMR for the crude sample of N-Acetyl cysteine (NAC) phosphorylated with POCl$_3$.
Figure 4:
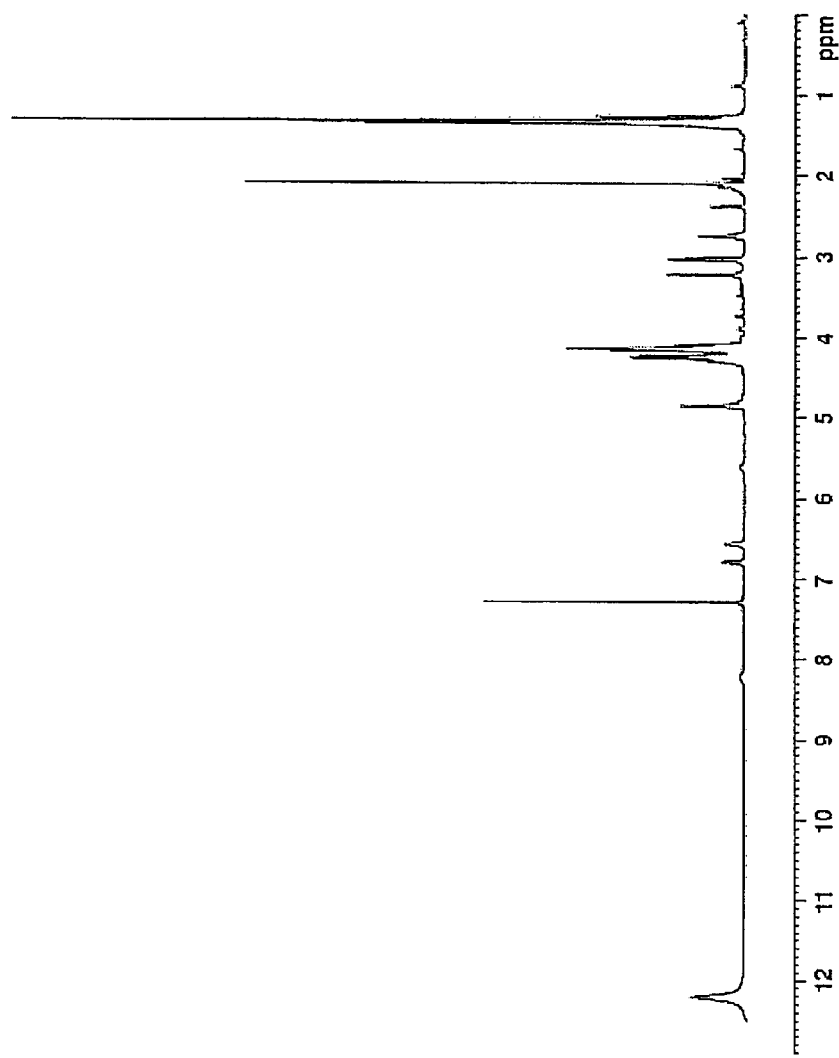
FIG. 4 is a $^1$H NMR for the crude sample of NAC phophorylated with POCL$_3$.
Figure 5:
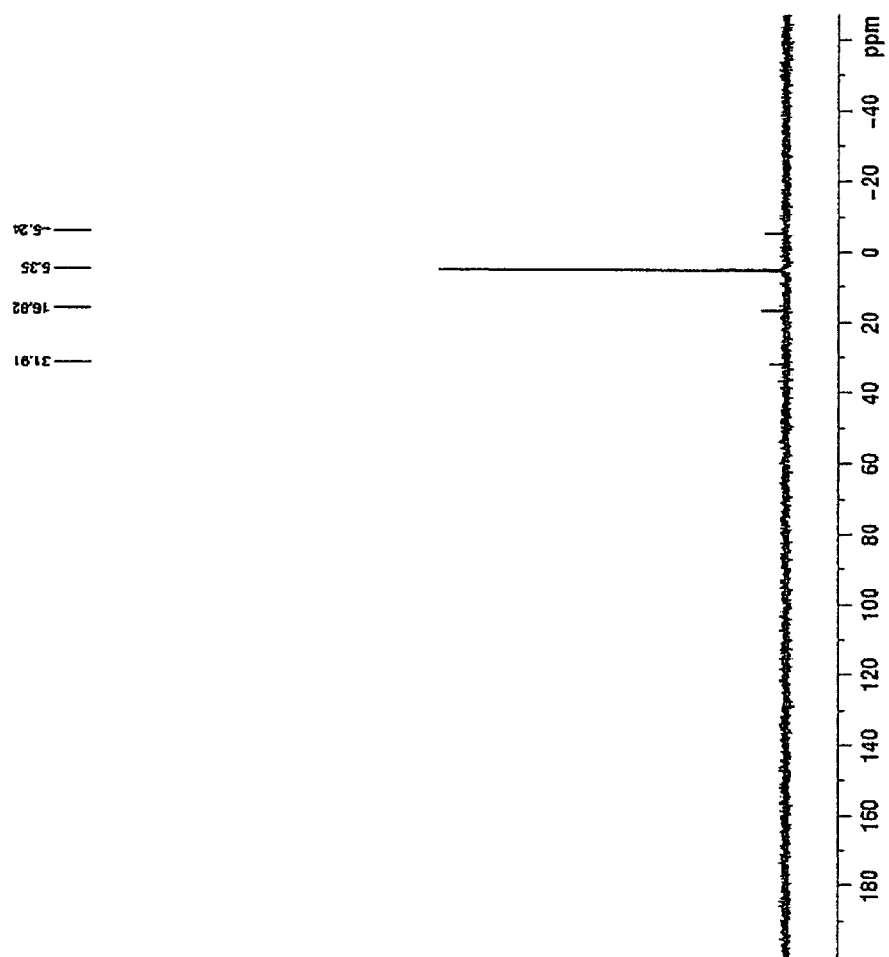
FIG. 5 is a $^{31}$P NMR for NAC phosphorylated with POCl$_3$ with the major peak at 5.35 ppm corresponding to POCl$_3$ and minor peak at −5.24 ppm corresponding to S—P linkage.
Figure 6:
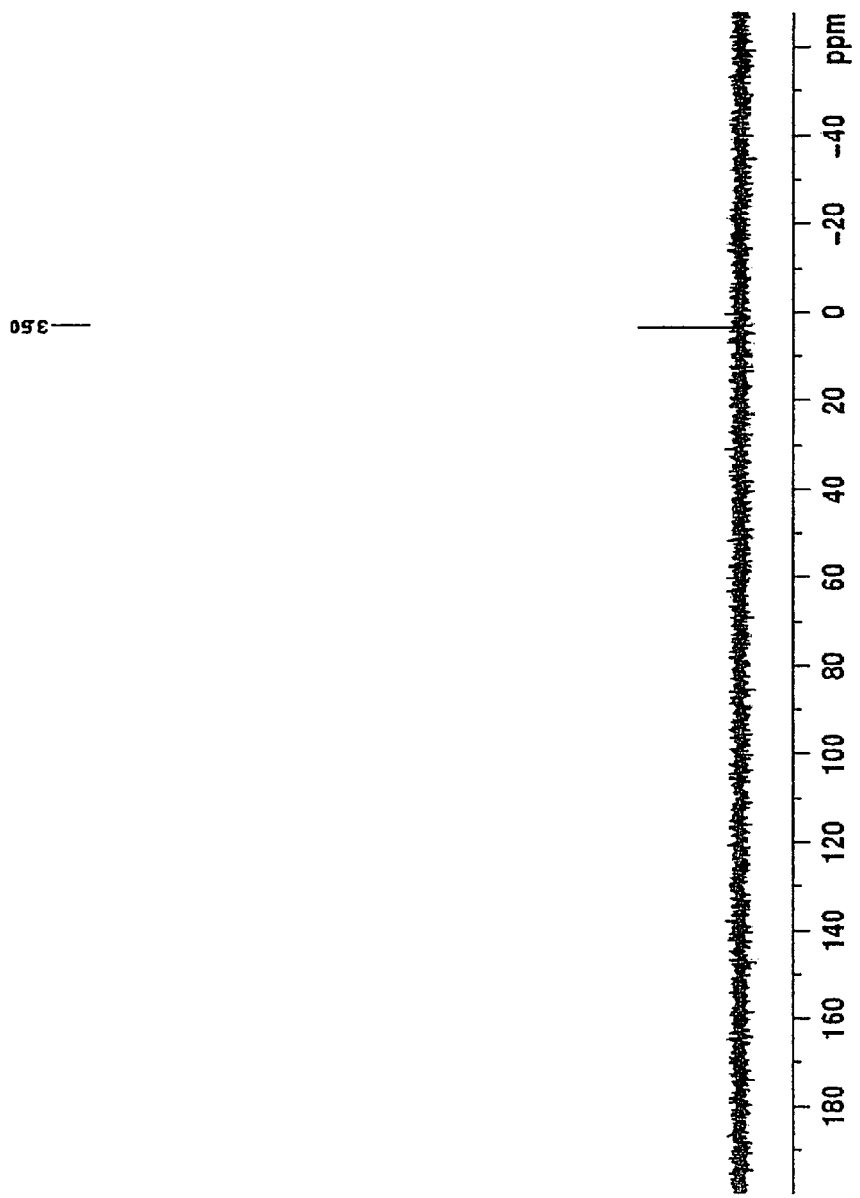
FIG. 6 is a $^{31}$P NMR spectrum for phosphorylated NAC on digestion with alkaline phosphatase, displaying a major peak at 3.50 ppm corresponding to free PO$_3^-$.

The phosphorylated NAC was analyzed with $^{31}P$ NMR. $^{13}C$ and $^{1}H$ were also performed but since the sample was crude, the carbon and proton NMR was not clear (FIGS. 3 and 4). The $^{31}P$ NMR showed a major peak at 5.3 ppm which corresponds to unreacted $POCl_3$ and minor peak at -5.2 ppm which, based on chemical shifts observed for O—P bond linkage (Burt et al, 1979; Silverstein, spectroscopic identification of organic compounds) can correspond to an S—P bond (FIG. 5). The phosphorylated sample was digested with alkaline phosphatase and analyzed with $^{31}P$ NMR, the spectrum displayed a single peak of free $PO_3^-$ at 3.0 ppm, indicating that the peak at -5.2 ppm was S—P linkage and was hydrolyzed with alkaline phosphatase (FIG. 6).

Example 2

Phosphorylation of Ester NAC

Synthesis of ester cysteine was followed according to the procedure as follows. NAC (0.2 g) was dissolved in 7 mL of ethanol, 2 mL of concentrated hydrochloric acid and stirred at room temperature for 1 hour. The reaction mixture was refluxed for 1 hour at 60° C. The sample was then dried and resuspended in acetonitrile for ESI-MS analysis (same instrument settings as described for analysis of HIDD). The acid protected sample was phosphorylated with $POCL_3$, and sodium hydroxide dried and resuspended in deuterium oxide for NMR analysis. After analysis, the sample was dried, resuspended in water, treated with 1 mg (10 units) of alkaline phosphatase and stirred for 2 hours. The product was dried, and resuspended in deuterium oxide for NMR analysis.

Figure 7:
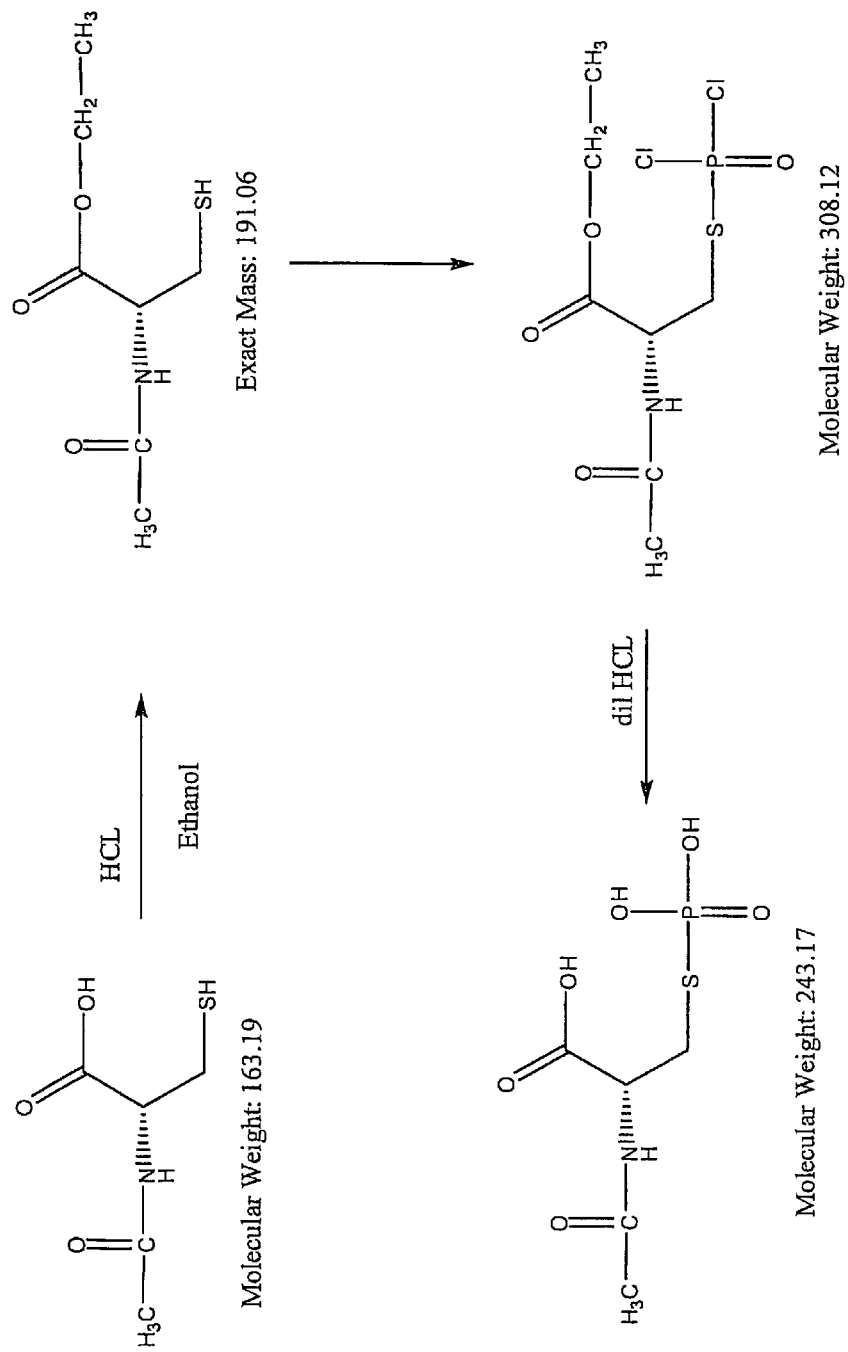
FIG. 7 is a reaction scheme for phosphorylation of acid protected NAC.
Figure 8:
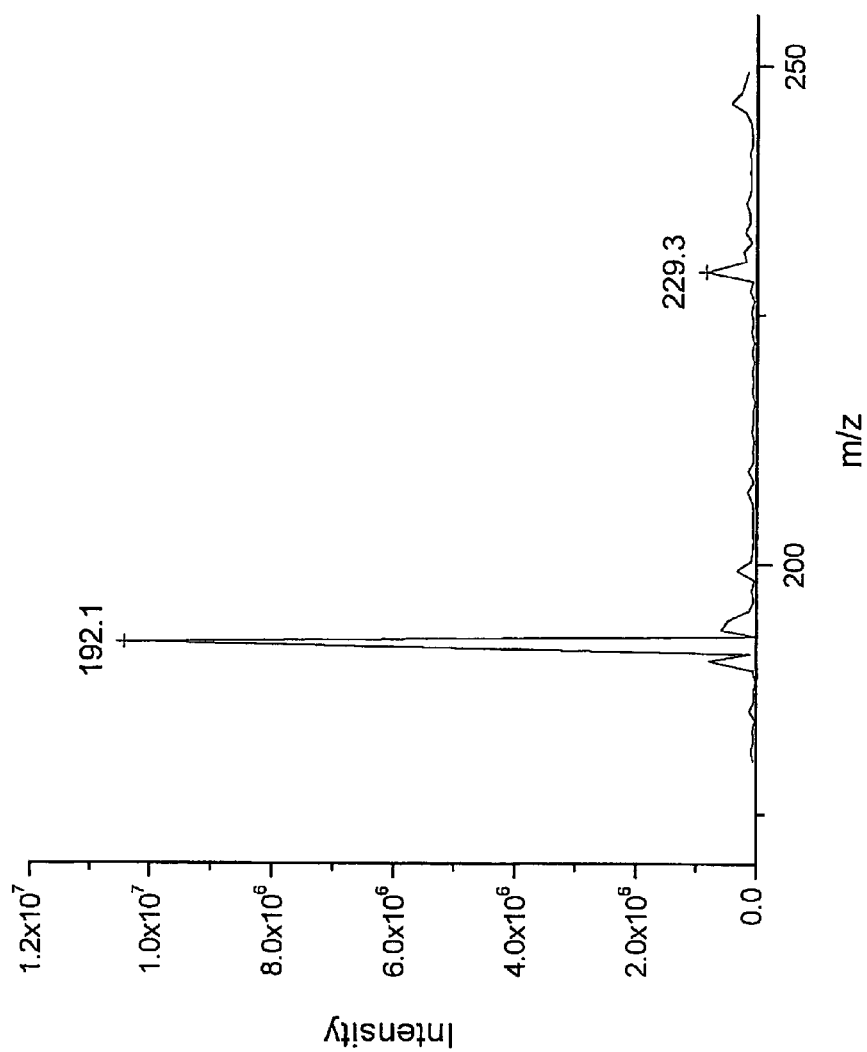
FIG. 8 is a full mass spectrum of acid protected NAC (m/z=191)
Figure 9:
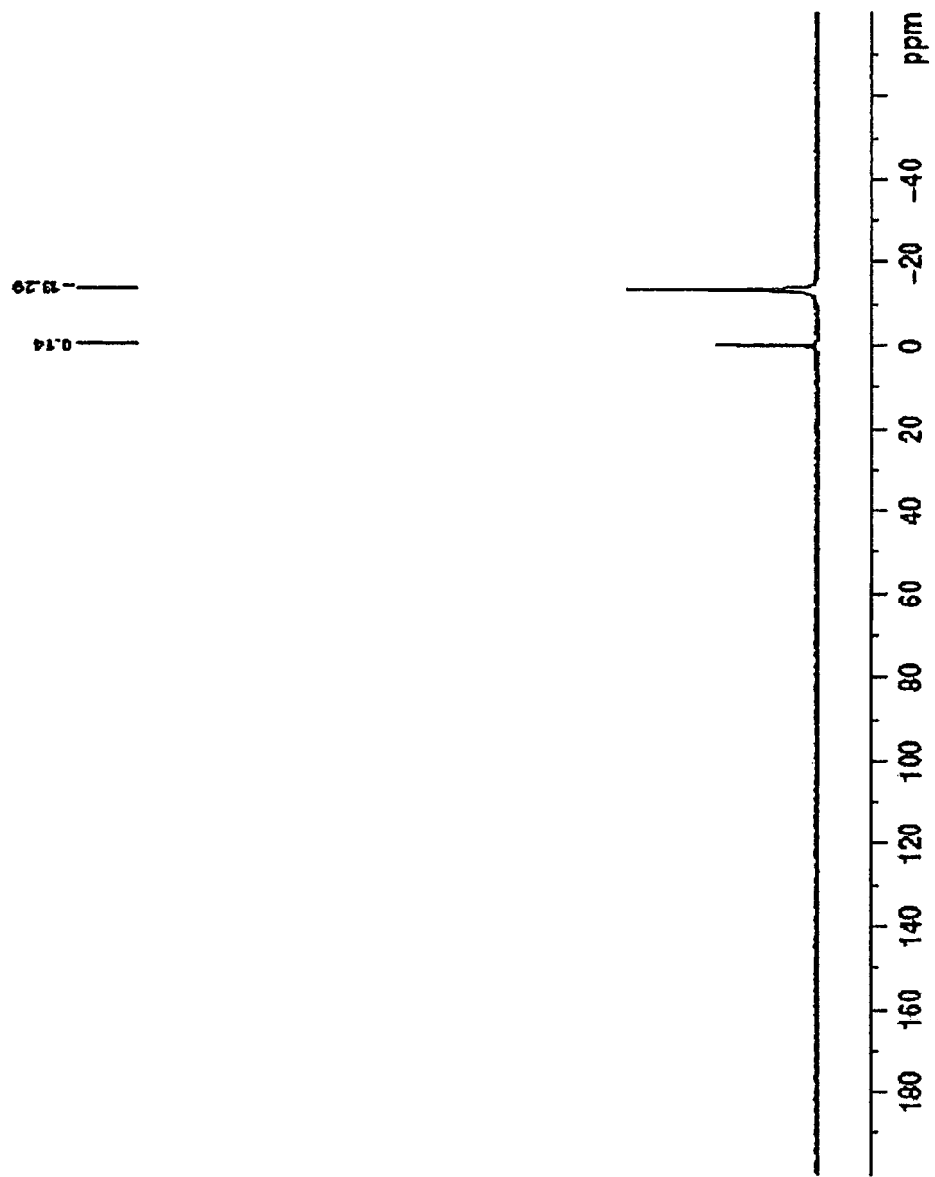
FIG. 9 is a $^{31}$P NMR spectrum for the drug WR-2721, chemical formula, H$_2$N(CH$_2$)$_3$HN(CH$_2$)$_2$SPO$_3$H$_2$, The peak at −13.2 ppm corresponds to S—P bond linkage.
Figure 10:
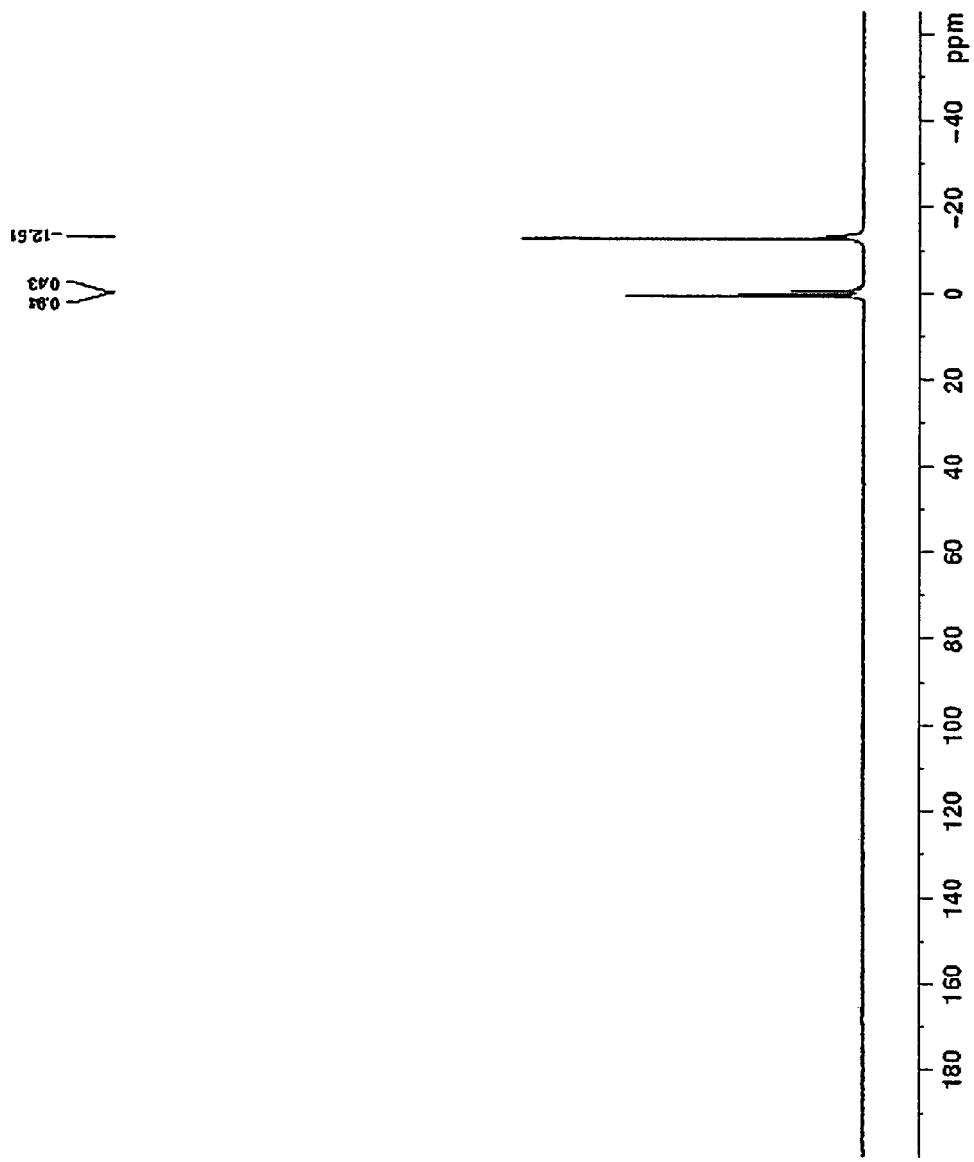
FIG. 10 is a $^{31}$P NMR spectrum for phosphorylated ester cysteine with major peak at 0.4 ppm corresponding to unreacted POCl$_3$, and −12.51 ppm which may correspond to S—P linkage.
Figure 11:
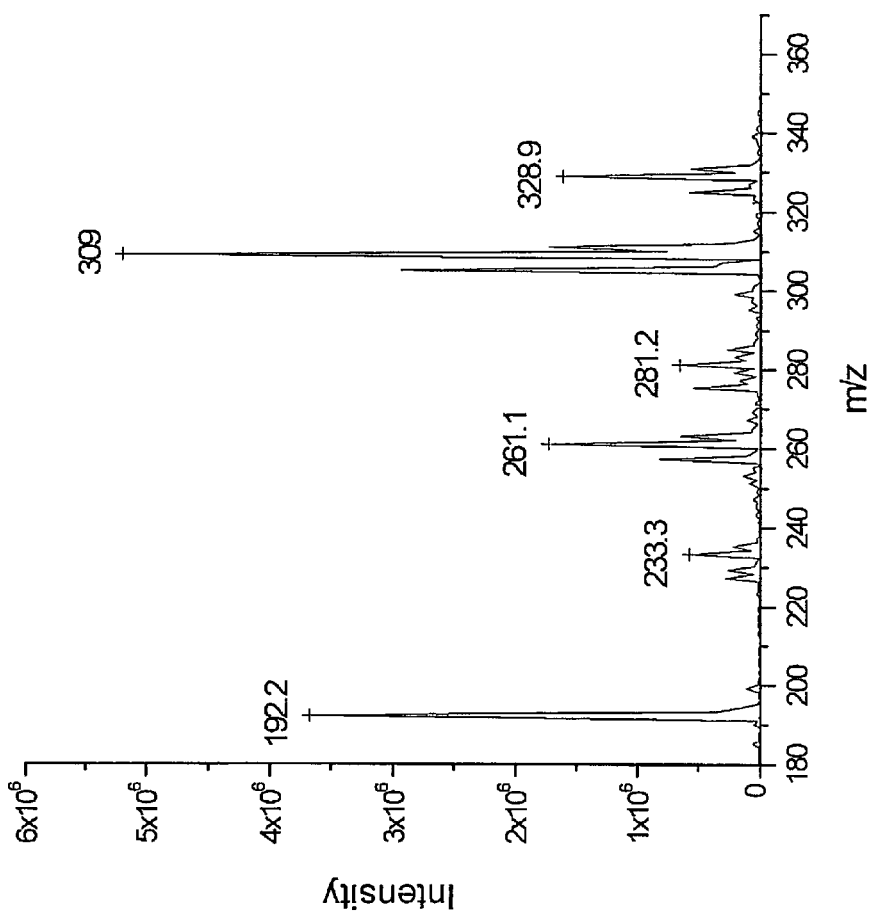
FIG. 11 is a full mass spectrum of acid protected NAC phosphorylated with POCl$_3$ (m/z=309)
Figure 12:
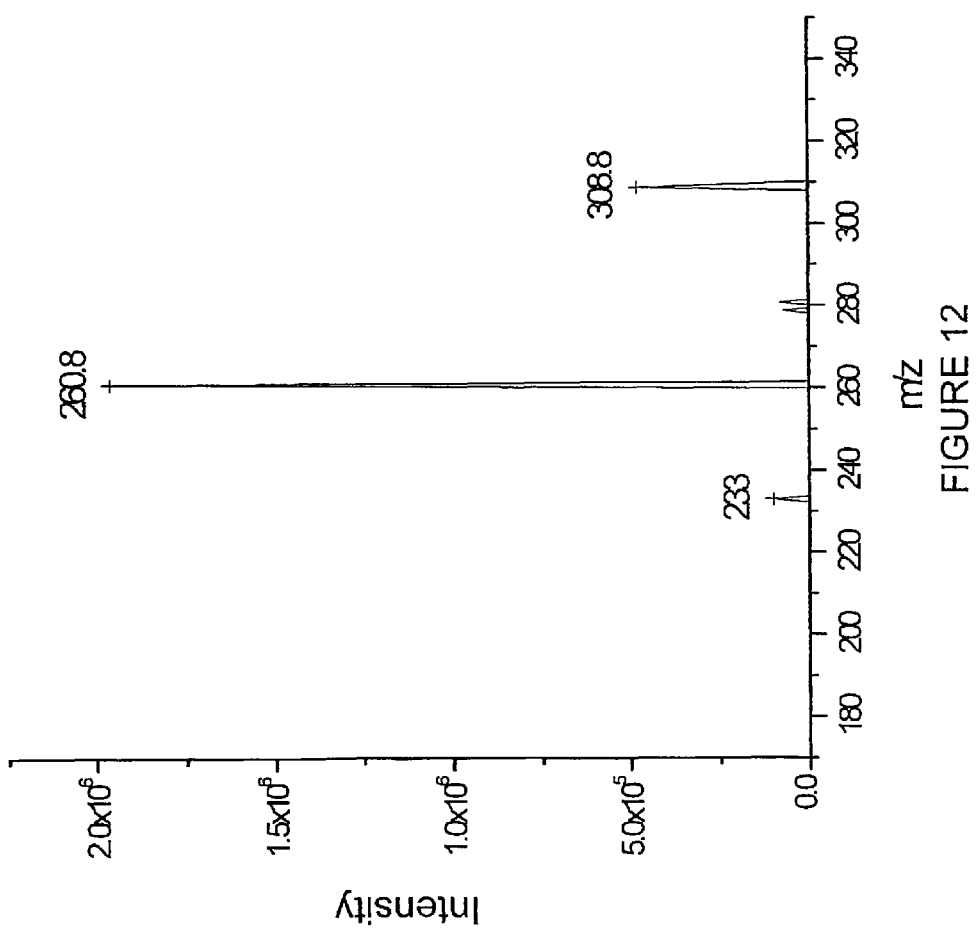
FIG. 12 is a CID spectrum for m/z=309 (collision energy 35%)
Figure 13:
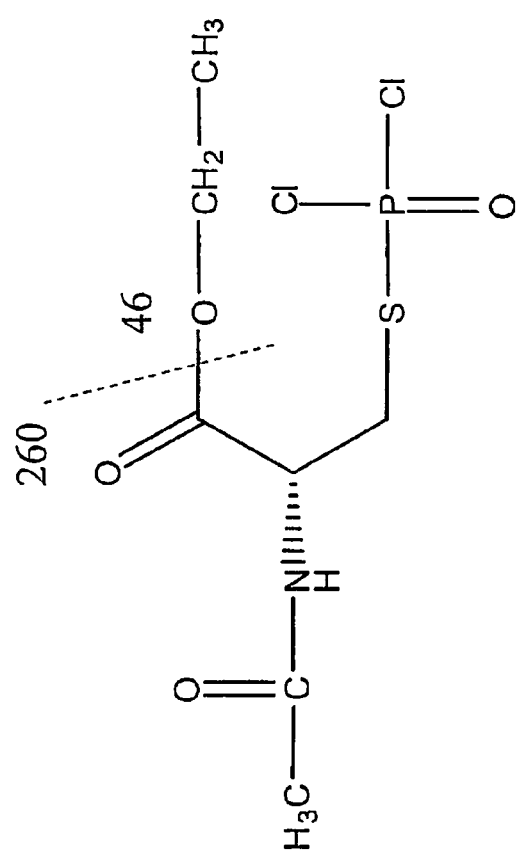
FIG. 13 is a representation of fragmentation resulting from phosphorylated ester cysteine, displaying the loss of ethanol group to give the major fragment with m/z −260.
Figure 14:
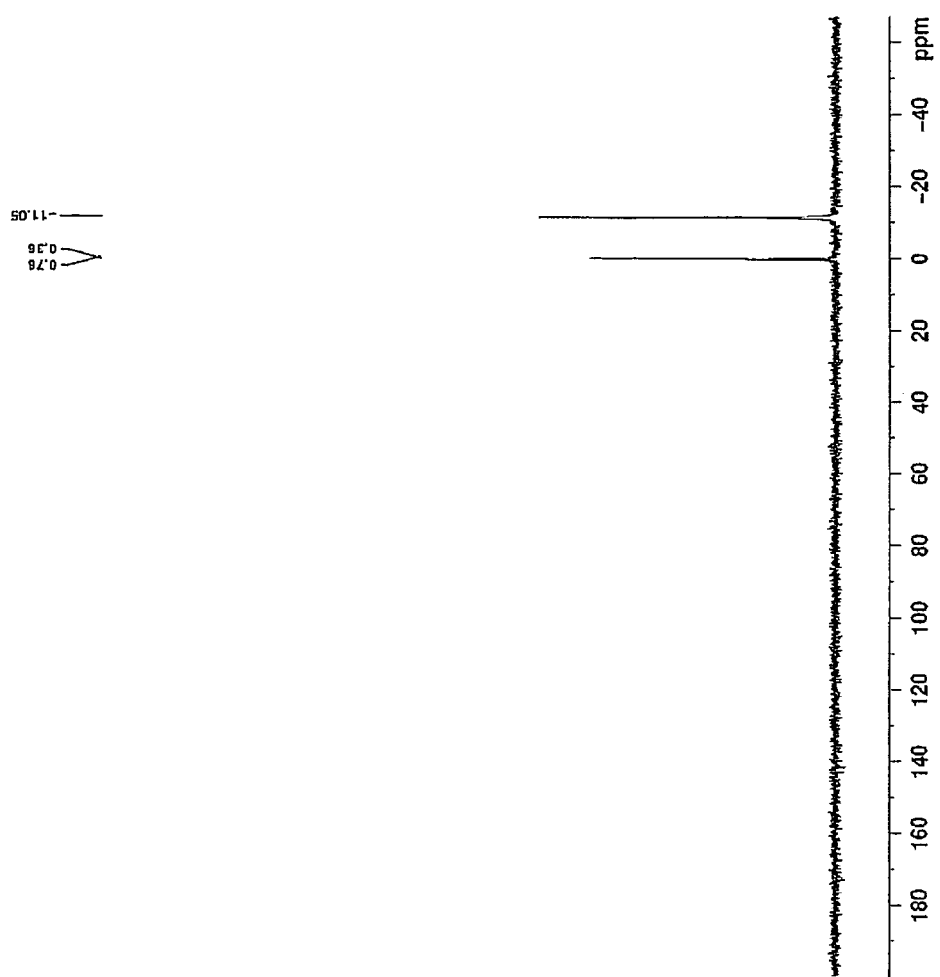
FIG. 14 is a $^{31}$P NMR spectrum for phosphorylated acid protected cysteine digested with alkaline phosphatase after 24 hours, and displays a decrease in intensity and a shift from −12 ppm to −11 ppm indicating the cleavage of S—P bond linkage and formation of free PO$_3$.
Figure 15:
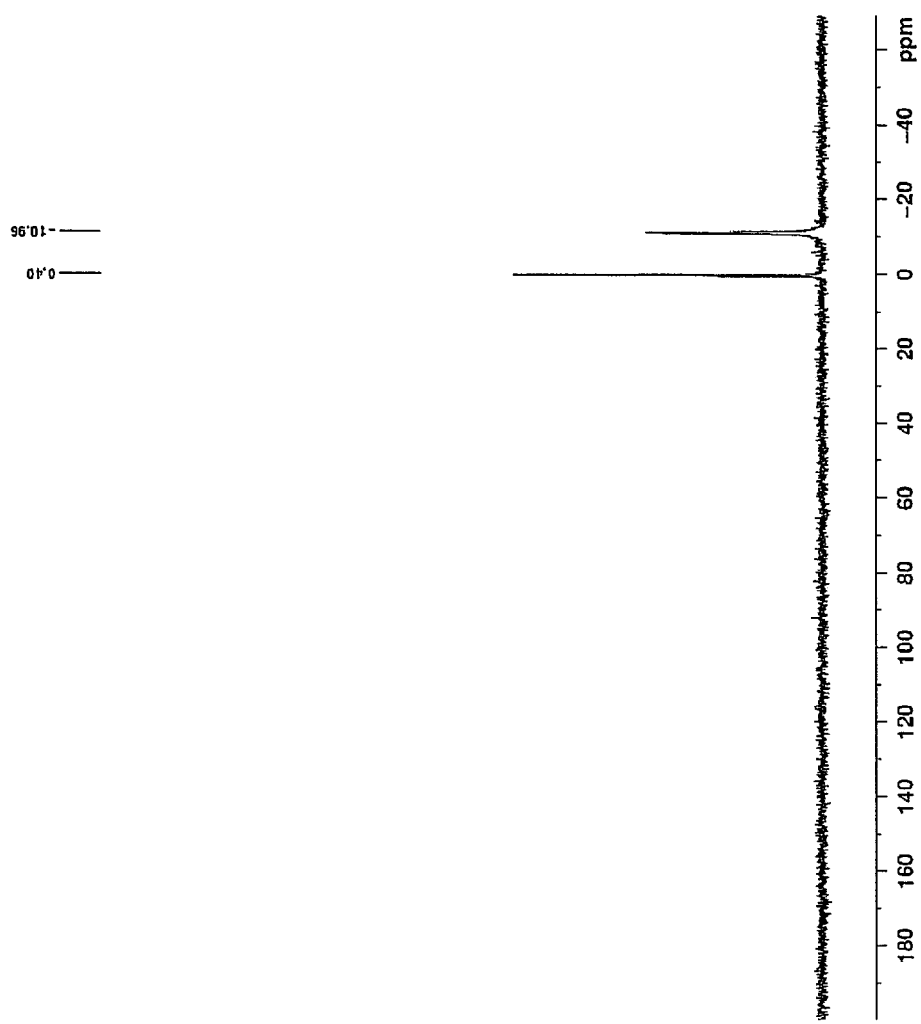
FIG. 15 is a $^{31}$P NMR spectrum for phosphorylated ester cysteine on digestion with alkaline phosphatase after 36 hours, displaying a decrease in intensity and chemical shift from −11 ppm to −10 ppm, indicating further cleavage of S—P bond and formation of free PO$_3$.

FIG. 7 gives the reaction scheme for the phosphorylation procedure. The ester cysteine was analyzed with ESI-MS. FIG. 8 displays the full mass spectrum of ester cysteine with m/z=191. Phosphorylation was done with phosphorus oxychloride and analyzed with $^{31}P$ NMR. The spectra displayed a major peak at -11.0 ppm which, based on analogy to the $^{31}P$ NMR spectra of the drug, WR-2721 $(H_2N(CH_2)_3HN(CH_2)_2SPO_3H_2)$ (FIG. 9), corresponds to S—P linkage and minor peaks of 0.4 ppm correspond to the unreacted $POCl_3$ (FIG. 10). The ESI-MS data displayed a mixture of compounds with a major peak of m/z=309 (FIG. 11), and CID spectrum of this compound displayed a major fragment of m/z=260 which can be attributed to loss of ethanol group (FIGS. 12 and 13). The sample was then treated with alkaline phosphatase and analyzed with $^{31}P$ NMR. The peak at -11 ppm showed time dependent decrease in intensity at 24 hours and 36 hours indicating cleavage of S—P linkage and increase in intensity for the free $PO_3^-$ peak (FIGS. 14 and 15).

Example 3

Phophorylation of Ester Cysteine with Diethyl Chlorophosphate (DECP)

The ester NAC was synthesized according to the procedure as follows and analyzed with ESI-MS. A 0.3 g of acid protected NAC was dissolved in 7 mL of chloroform. Triethylamine (0.4 mL) was added to the reaction mixture and stirred for 1 hour. The flask was placed in an ice bath while adding diethyl chlorophosphate drop wise to maintain a constant pH of 11. The mixture was stirred overnight at room temperature and later extracted with ethyl acetate, brine solution, and sodium sulfate. The product was dried and resuspended in chloroform, treated with 600 mg (10 equivalents) of TBMSBr, and stirred for approximately 6 hours. The final product was extracted with water, dried and re-suspended in deuterium oxide for NMR analysis. After analysis the sample was dried, resuspended in water, and treated with 1 mg (10 units) of alkaline phosphatase and stirred for 2 hours. The solution was then dried and resuspended in deuterium oxide for NMR analysis.

Figure 16:
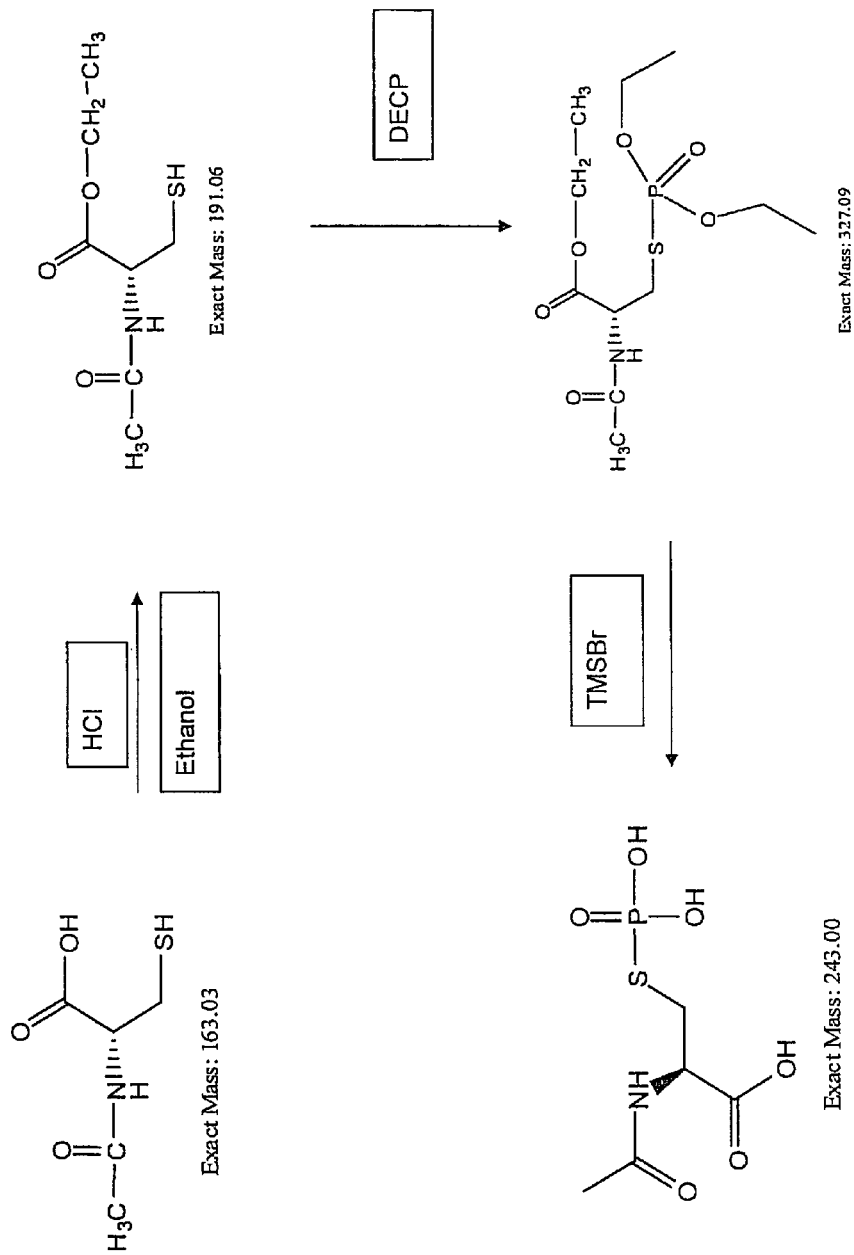
FIG. 16 is a reaction scheme for phophorylation of acid protected NAC with DECP.
Figure 17:
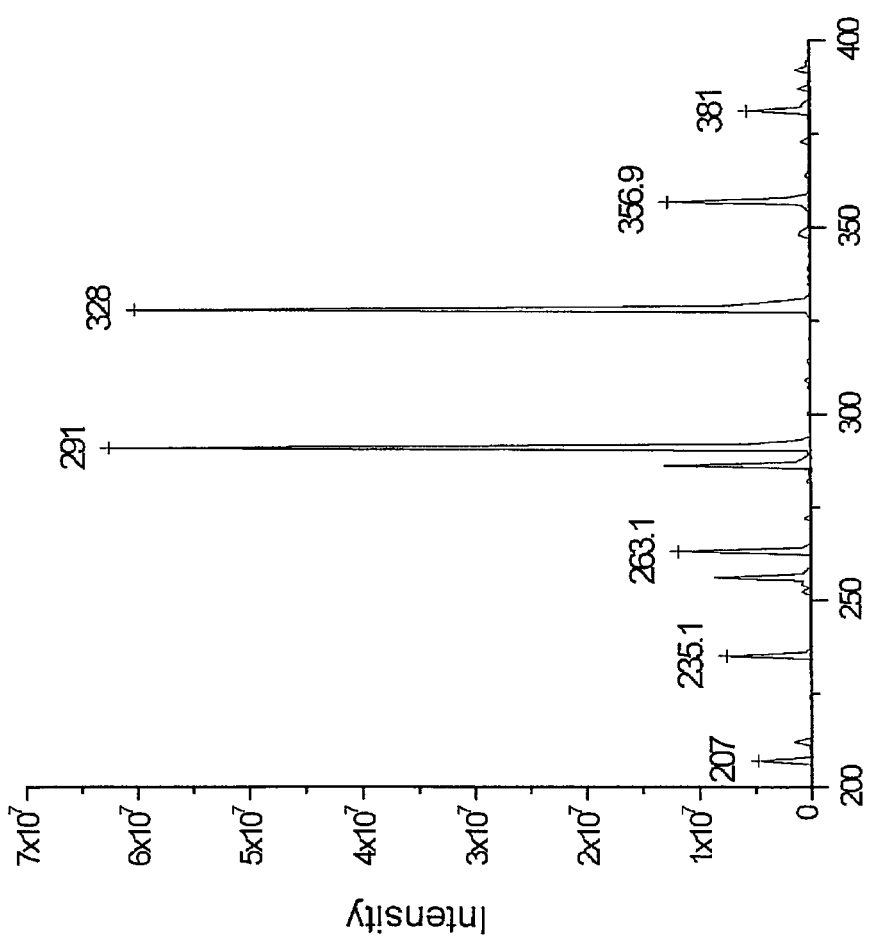
FIG. 17 is a full mass spectra of the crude sample from acid protected NAC phosphorylated with DECP (m/z=328)
Figure 18:
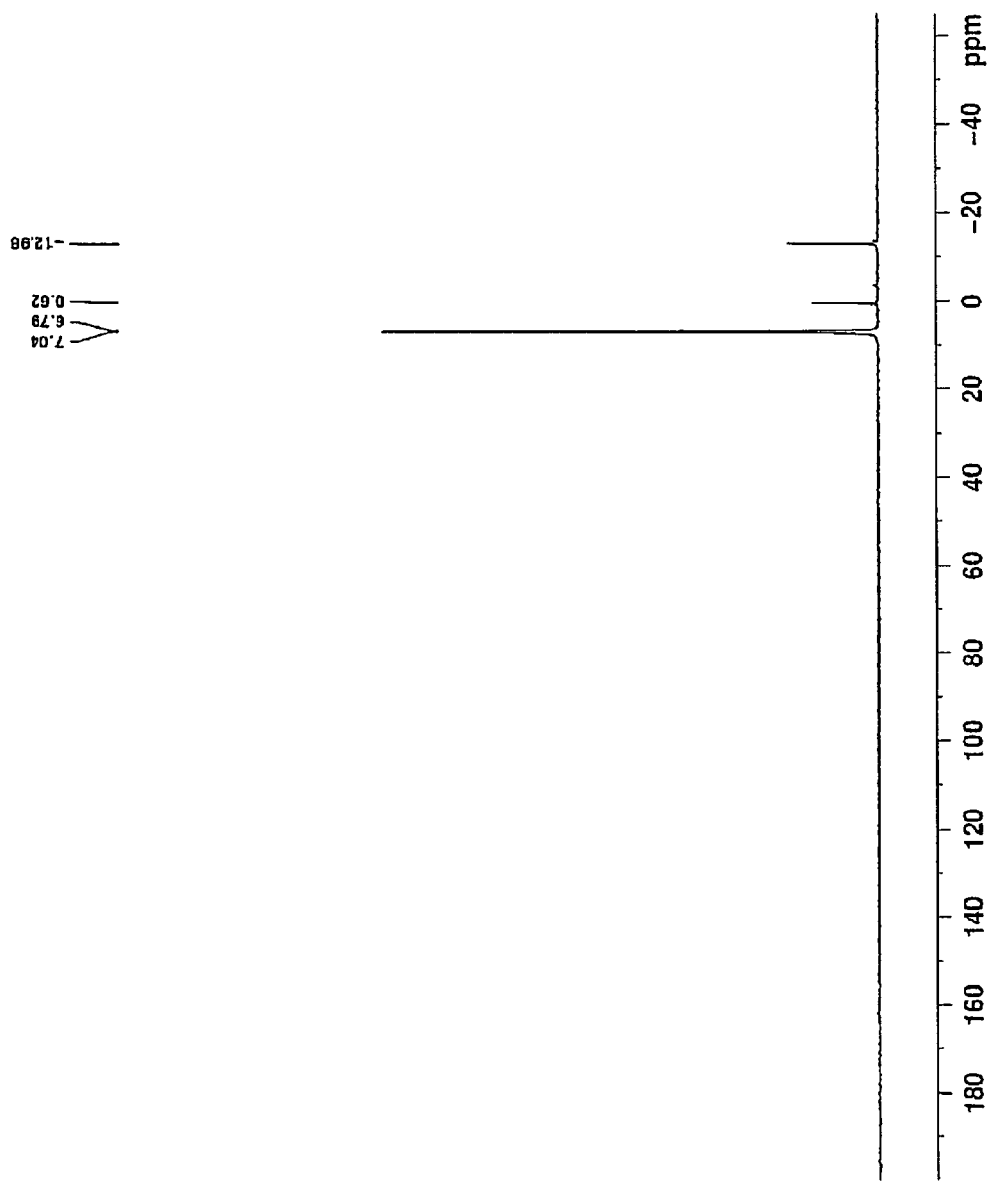
FIG. 18 is a $^{31}$P NMR spectrum for ester NAC phosphorylated with DECP, displaying a major peak at 7.0 ppm corresponding to unreacted DECP and a minor peak at −12.9 ppm corresponding to S—P linkage.
Figure 19:
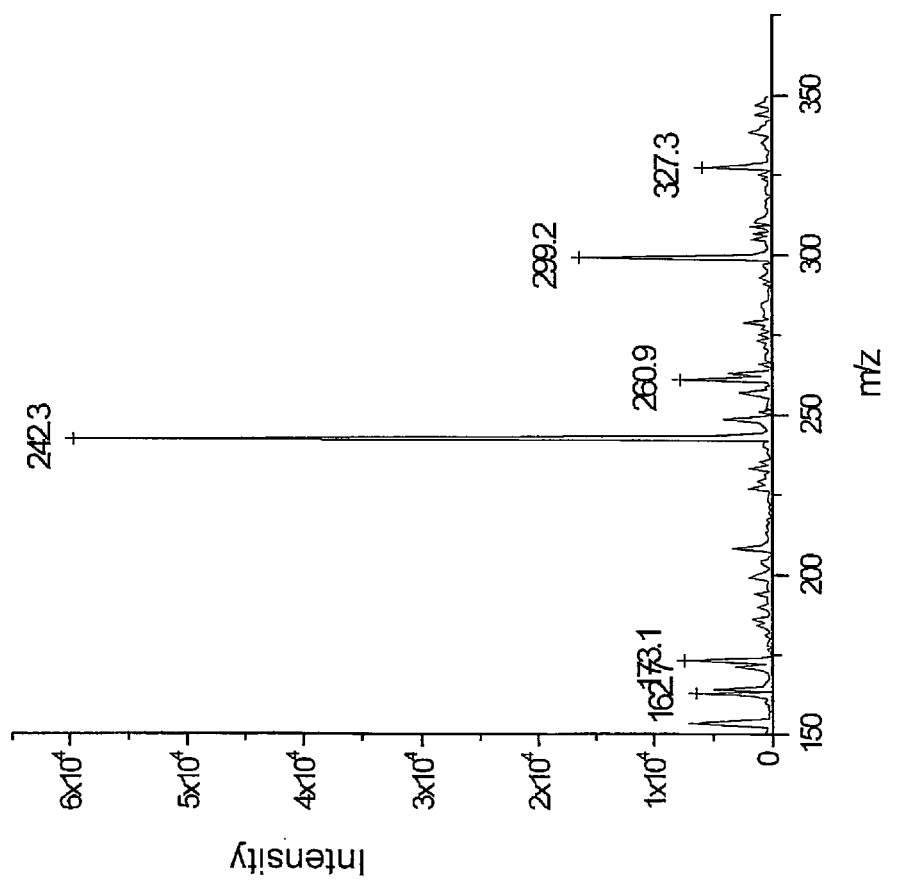
FIG. 19 is a full mass spectrum of ester NAC phosphorylated with DECP after TMSBr reaction (m/z=242.3)

The sample was phosphorylated with DECP and analyzed with $^{31}P$ NMR spectroscopy. FIG. 16 illustrates the reaction scheme followed for the phosphorylation procedure. The ESI-MS spectra showed a mixture of compounds, the phosphorylated ester cysteine with m/z=328 (FIG. 17). The phosphorus NMR showed a major peak at 7 ppm, which corresponds to unreacted DECP and minor peak at -12.9 ppm, which can correspond to S—P bond linkage (based on anology to WR-2721) (FIG. 18). The sample was then treated with TMSBr, to cleave the ethyl groups on the phosphate and NAC. The ESI-MS analysis of the crude sample showed mixture of peaks, the peak with m/z=242 corresponds to phosphorylated ester cysteine with hydrolyzed ethyl groups (FIG. 19). $^{31}P$ NMR spectrum showed major peak at 0.2 ppm, which can correspond to the unreacted DECP with hydrolyzed ethyl groups and a minor peak at -10.8 ppm, which can correspond to the S—P bond linkage (FIG. 20). The sample was digested with alkaline phosphatase and analyzed with $^{31}P$ NMR. The spectrum showed a single peak at 0.2 ppm, indicating the hydrolysis of S—P linkage and presence of free $PO_3^-$ moiety (FIG. 21).

The above examples show that phosphorylated prodrugs were effectively created that can be used to increase bioavailability of the drugs to provide antioxidant activity for a wide variety of applications where ROS damage is unwanted.

The invention has been described in an illustrative manner, and it is to be understood that the terminology which has been used is intended to be in the nature of words of description rather than of limitation.

Obviously, many modifications and variations of the present invention are possible in light of the above teachings.

It is, therefore, to be understood that the invention may be practiced otherwise than as specifically described.

What is claimed is:

1. A prodrug comprising

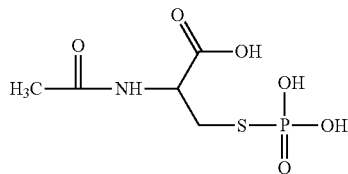

or esters thereof.

2. A prodrug comprising a phosphorylated cysteine of the formula

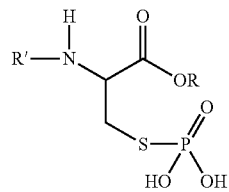

wherein R' is an acyl, and
wherein R is H or an alkyl group,
wherein the prodrug has antioxidant activity.

3. A prodrug comprising a phosphorylated cysteine of the formula

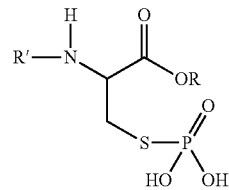

wherein R' is H or an acyl, and
wherein R is an alkyl group,
wherein the prodrug has antioxidant activity.

4. The prodrug of claim 3, wherein the alkyl group is methyl, butyl, propyl, isopropyl, or isobutyl.

5. The prodrug of claim 3, wherein the acyl is acetyl.

6. The prodrug of claim 2, wherein the alkyl group is methyl, butyl, propyl, isopropyl, or isobutyl.

7. The prodrug of claim 2, wherein the acyl is acetyl.

* * * * *